United States Patent
Boguszewski et al.

(12) 
(10) Patent No.: US 6,639,675 B1
(45) Date of Patent: Oct. 28, 2003

(54) METHOD AND APPARATUS FOR ALIGNING A MIRROR OF A CARBON IN FLY ASH SENSOR

(75) Inventors: Stanley J. Boguszewski, Russell, MA (US); Joseph W. Quinn, Bloomfield, CT (US)

(73) Assignee: ABB Automation Inc., Wickliffe, OH (US)

( * ) Notice: Subject to any disclaimer, the term of this patent is extended or adjusted under 35 U.S.C. 154(b) by 505 days.

(21) Appl. No.: 09/660,067

(22) Filed: Sep. 12, 2000

(51) Int. Cl.[7] ............... G01B 11/00; G01N 31/00; G01N 7/00
(52) U.S. Cl. ............... 356/399; 356/400; 702/24; 73/23.33
(58) Field of Search ............... 702/24, 23, 25, 702/26, 28; 324/633, 637; 431/76; 700/274; 73/23.31, 23.33, 28.01; 356/399–401

(56) References Cited

U.S. PATENT DOCUMENTS

| | | | | |
|---|---|---|---|---|
| 4,043,743 A | * | 8/1977 | Seider | 431/76 |
| 4,286,876 A | * | 9/1981 | Hogg et al. | 356/343 |
| 5,206,176 A | * | 4/1993 | Beer et al. | 436/140 |
| 5,729,470 A | * | 3/1998 | Baier et al. | 702/24 |
| 6,490,909 B1 | * | 12/2002 | Boguszewski et al. | 73/23.33 |

* cited by examiner

Primary Examiner—Russell Adams
Assistant Examiner—Andrew Sever
(74) Attorney, Agent, or Firm—Michael M. Rickin

(57) ABSTRACT

A method and apparatus for aligning the axis of a mirror of a carbon in ash sensor. The method first executes a series of steps that causes a stepper motor connected to an axis of the mirror to move the mirror through a first coarse alignment procedure and then executes a second series of steps that that moves the mirror through a second fine alignment procedure.

27 Claims, 6 Drawing Sheets

METHOD AND APPARATUS FOR ALIGNING A MIRROR OF A CARBON IN FLY ASH SENSOR

FIELD OF THE INVENTION

This invention relates to sensors that measure the Carbon content of the fly ash produced by the combustion process in a pulverized coal-fired steam generator and more particularly to the alignment of the mirrors used in such a sensor.

DESCRIPTION OF THE PRIOR ART

Fly ash results from the incomplete combustion of pulverized coal in a pulverized coal-fired steam generator. The fly ash is the combination of inert and inorganic residue resulting from the incomplete combustion of the pulverized coal. The pulverized coal contains varying amounts of carbon or coke particles. In general, the inorganic ash particles consist primarily of silicates, oxides and sulfates, together with small quantities of phosphates and other trace compounds.

The presence of unburned Carbon in boiler fly ash has important economic and environmental consequences to the operator of a coal-fired boiler installation. Its presence is a measure of inefficient fuel utilization which means that more fuel must be burned in order to obtain a given output and which in turn directly increases the cost of electrical power generation. Furthermore, inefficient fuel utilization by virtue of requiring more fuel to be burned in order to produce a given output increases the presence of $NO_x$ emissions which is the basis for environmental concerns. Thus, knowledge of the Carbon content of boiler fly ash is an important element in establishing a low $NO_x$ boiler emission strategy.

In addition, low Carbon fly ash can be a potential source of income to the operator of a pulverized coal-fired boiler in that fly ash can be employed as a building material if the Carbon content in the fly ash is sufficiently low. Fly ash with a high Carbon content is unsuitable as a building material and normally requires the use of expensive waste disposal methods.

One system for continuous in-situ measurement of Carbon in fly ash is described in U.S. Pat. No. 5,729,470 ("the '470 patent") which is assigned to the same assignee as the present invention. The system described in the '470 patent includes a resonant cavity for measuring in-situ and in real time the Carbon content of the fly ash.

Referring now to FIG. 1 (which is FIG. 5 of the '470 Patent), there is shown the resonant cavity 300 in the system of the '470 patent. Also shown in FIG. 1, are intelligence 100, transmitting section 200 and receiving section 400 of the system of the '470 patent. As is shown in FIG. 2 herein (which is FIG. 3 of the '470 Patent), intelligence 100 includes a CPU 112.

Returning once again to FIG. 1, the transmitting section 200 includes a pressure boundary 202, an oscillator 204, a signal coupler 208, a reference detector 210, a signal isolator 214 and a waveguide 216.

The transmitting section 200 further includes a first air purge 218 and a second air purge 220.

The cavity section 300 is comprised of a first concave spherical mirror 302, a second concave spherical mirror 304, a common optical axis 306, a plurality of alignment screws 308, an inspection volume 300', a first annular ring 302' and a second annular ring 304'. As is shown in FIG. 3 (which is FIG. 6 of the '470 patent) the first and second concave spherical mirrors 302, 304 each contain a pattern of circular holes that are drilled therethrough that consist of a central hole 310, so located as to be on the optical axis 306, which is common both to the first concave spherical mirror 302 and the second concave spherical mirror 304 and an array of planetary holes 312 symmetrically located about the central hole 310.

As is shown in FIG. 4 (which is FIG. 7 of the '470 patent) the first and second concave spherical mirrors 302, 304 have attached to their nonreflecting sides three screws 308 symmetrically located about the center of the mirrors 302, 304 for the purpose of aligning said mirrors 302, 304 along the common optical axis 306. Two of three alignment screws 308 for each of mirrors 302, 304 are turned by an associated stepper motor. FIG. 1A, which is an enlargement of a portion of FIG. 1, shows the stepper motor 320 connected to one of the alignment screws 308. The motor 320 has a hollow shaft with internal threads and is threaded onto the associated alignment screw 308. The motor 320 is controlled by CPU 112 of intelligence 100.

The receiving section 400 includes a pressure boundary 402, a waveguide 404 and a signal detector 408.

The receiving section 400 further includes a first air purge 412 and a second air purge 414.

The oscillator 204 receives as input the electrical drive signal 104 originating from the intelligence section 100. The oscillator 204 typically may take the form of a free running biased tuned microwave oscillator, the nature of the construction and the mode of operation of which is known and understood by those skilled in the art. As a consequence of the input received thereby, the oscillator 204 generates as output a constant amplitude, sinusoidal signal 206 of electromagnetic radiation which repeatedly sweeps through a certain frequency span, $\Delta f$.

The oscillator output signal 206 is supplied in known fashion to the signal coupler 208. Again in known fashion, a small fraction 206' of the oscillator output signal 206 is diverted by the signal coupler 208 to the reference detector 210, to be described hereinafter, and the remainder 206" of the oscillator output signal 206 is supplied to the waveguide 216 via the signal isolator 214. Typically the signal isolator 214 may take the form of a waveguide section filled with a ferrite material so aligned that in combination with the magnetic field of a permanent magnet, electromagnetic radiation can propagate in one direction only. The purpose of the signal isolator 214 is to prevent signal return from the cavity section 300. Since reflected energy is sharply attenuated by the signal isolator 214 it helps ensure the frequency and amplitude stability of the oscillator 204.

The detector 210 is designed to receive as input the signal 206' which is delivered from the signal coupler 208 in the form of electromagnetic radiation and whose power is a small fraction of the oscillator signal 206 power. The reference detector 210 typically may take the form of a full wave rectifier which may or may not be followed by a peak detector. The reference detector 210 is operative upon the input signal 206' in a known manner in order to thereby generate as output a reference signal 212 in the nature of a DC voltage proportional to the power of the input signal 206' that is supplied to the reference detector 210.

The signal 206" in the form of electromagnetic radiation is supplied as an input to the waveguide 216 which, in accordance with the best mode embodiment of the invention, is rigidly fixed to the non-reflecting side of the first concave spherical mirror 302 so as to be aligned along the common optical axis 306. The waveguide 216 in turn is designed so as to be operative to deliver the signal 206" to the cavity section 300 via the central hole 310 which is illustrated in FIG. 3. The waveguide 216, in accordance with the best mode embodiment of the invention, is preferably equipped with a first air purge 218. The air purge 218 is designed to be operative so as to direct an external source of pressurized air 218' into and along the waveguide 216 through to the cavity section 300 via the central hole 310 depicted in FIG. 3. Such purging activity helps prevent fouling of the mirror 302 and the waveguide 216 which might otherwise occur due to fly ash buildup.

The transmitting section 200 includes a pressure boundary 202. The pressure boundary 202 may or may not enclose the oscillator 204, the signal coupler 208, the reference detector 210 and the signal isolator 214. The pressure boundary 202 coupled with the first spherical mirror 302 and an annular ring 302' concentric with the mirror 302 is intended to define a volume 202' which undergoes purging similar to that which has been described above. Such purging directs an external source of pressurized air 220' into the aforesaid volume 202' through to the cavity section 300 via the annular ring 302' and the planetary holes 312 shown in FIG. 3. The purging activity helps prevent fouling of the mirror 302 which might otherwise occur due to fly ash buildup.

The cavity section 300 includes the first concave spherical mirror 302 and the second concave spherical mirror 304, each aligned along the common optical axis 306 and so oriented that their reflective sides face one another. For purposes of the description thereof the cavity section 300 further is considered to encompass the approximately cylindrical inspection volume 300' subtended by the concave spherical mirrors 302, 304, as the latter are separated by a fixed distance, L, along the common optical axis 306, and an imaginary boundary not shown in FIG. 1 but shown in FIG. 9 of the '470 patent delimited by the beam spot size, $w(z)$. It is through and across this inspection volume 300' that the flue gas stream 28 is made to flow, carrying with it boiler fly ash.

As described hereinabove, the sinusoidal signal 206" of electromagnetic radiation is supplied to the cavity section 300 from the transmitting section 200 via the waveguide 216. The signal 206" enters the inspection volume 300' from the center hole 310 depicted in FIG. 3. The signal 206" propagates through the inspection volume 300' to the second concave spherical mirror 304 and is reflected back to the first concave spherical mirror 302 to be reflected once again back to the second concave spherical mirror 304. To this end the signal 206" is reflected back and forth between the two spherical mirrors 302, 304 numerous times. The resulting steady state signal 206" is captured by the second concave spherical mirror 304 at the center hole 310 shown in FIG. 3. The signal 206" is then delivered by way of the waveguide 404 to the signal detector 408. The waveguide 404, in accordance with the best mode embodiment of the invention, preferably is rigidly fixed to the non-reflecting side of the second concave spherical mirror 304 so as to be aligned along the common optical axis 306.

The signal detector 408 receives as input, from the cavity section 300, the signal 206" that is in the form of electromagnetic radiation. Typically the signal detector 408 may take the form of a full wave rectifier which may or may not be followed by a peak detector. The signal detector 408 is operative upon the input signal 206" in known fashion to provide as an output therefrom, a cavity signal 410 which is in the nature of a DC voltage that is proportional to the power of the input signal 206" to the signal detector 408. The cavity signal 410 then functions as one input to the intelligence section 100.

It is further seen from reference to FIG. 1 that the receiving section 400 includes a pressure boundary 402. The pressure boundary 402 may or may not enclose the signal detector 408. The pressure boundary 402 coupled with the second concave spherical mirror 304 and an annular ring 304', concentric with the second concave spherical mirror 304, define a volume 402' which, preferably in accordance with the best mode embodiment of the invention, undergoes purging from an external source of pressurized air 414' similar to that which has been described hereinabove, with respect to the transmitting section 200. Furthermore, the waveguide 404 that directs the captured signal 206" to the signal detector 408 also, preferably in accordance with the best mode embodiment of the invention, undergoes a purging process from an external source of pressurized air 412' similar to that which has been described hereinabove, with respect to the transmitting section 200. Such purging helps prevent fouling of the mirror 304 and waveguide 404 as a result of fly ash buildup, which might otherwise occur.

The component elements of the resonant cavity are affixed to the rear gas pass of the pulverized coal-fired steam generator by rigidly fixing the pressure boundaries 202, 402 by any type of conventional means suitable for use for such purpose, to the opposing walls of the rear gas pass at nearly the same elevation. The first and second concave spherical mirrors 302, 304 of the cavity section 300 are in turn mounted to the pressure boundaries 202, 402 via the alignment screws 308 so as to be capable of mutual alignment along the common optical axis 306 by way of the alignment screws 308. It should be noted that the first and second concave spherical mirrors 302, 304 are not affixed directly to the walls of the rear gas pass.

As is described in detail in the '470 patent, the width of the cavity 300 is governed by the length of the rear gas pass and the ratio of the cavity width to the radius of curvature of mirrors 302, 304 is chosen based upon consideration of well established practice so as to ensure resonant cavity stability. As is described in the '470 patent, with this ratio and a first estimate of frequency the minimum beam spot size can be calculated and that minimum spot size is then used to find the diameter of the mirrors 302, 304.

As can be appreciated the accuracy of the measurement of the amount of Carbon in fly ash that is made by the sensor of the '470 patent depends on the alignment of the concave spherical mirrors 302, 304. It has been found that the change in dimensions of the pulverized coal-fired steam generator dimensions change with temperature affects the alignment of mirrors 302, 304. Therefore it is desirable to ensure that the mirrors are in proper alignment when the steam generator is operating.

SUMMARY OF THE INVENTION

A method for aligning the first axis of a first mirror of a sensor. The method has the steps of:

a) determining when the first mirror is in a first location which is a first predetermined number of steps in a first direction from a starting point for the first mirror the average peak amplitude of a signal received at a receiver connected to the first mirror;

b) moving the first mirror in a second direction which is opposite to the first direction in first increments each of a second predetermined number of steps and determining the average peak amplitude of the signal received at the receiving section at each of the first increments;

c) stopping movement of the first mirror in the second direction when the first mirror has moved a predetermined number of the first increments beyond the starting point;

d) determining the first increment where the average peak amplitude of the received signal was the highest and moving the first mirror to the determined first increment;

e) moving the first mirror the second predetermined number of steps in the first direction to a second location and determining the average peak amplitude of the signal received at the receiving section at the second location;

f) moving the first mirror in the second direction in second increments each of a third predetermined number of steps and determining the average peak amplitude of the signal received at the receiving section at each of the second increments;

g) stopping movement of the first mirror in the second direction when the first mirror has moved beyond the determined first increment a predetermined number of the second increments; and h) determining the second increment where the average peak amplitude of the received signal was the highest and moving the first mirror to the determined second increment.

A method for aligning the axis of a mirror of a sensor. The method has the steps of:

a) moving the mirror from a starting point a first predetermined number of steps in a first direction to a first location;

b) determining when the mirror is in the first location the average peak amplitude of a signal received at a receiver connected to the mirror;

c) moving the mirror in a second direction which is opposite to the first direction in first increments each of a second predetermined number of steps and determining the average peak amplitude of the signal received at the receiving section at each of the first increments;

d) stopping movement of the mirror in the second direction when the mirror has moved a number of the first increments beyond the starting point equal to the first predetermined number of steps;

e) determining the first increment where the average peak amplitude of the received signal was the highest and moving the mirror to the determined first increment;

f) moving the mirror the second predetermined number of steps in the first direction to a second location and determining the average peak amplitude of the signal received at the receiving section at the second location;

g) moving the mirror in the second direction in second increments each of a third predetermined number of steps and determining the average peak amplitude of the signal received at the receiving section at each of the second increments;

h) stopping movement of the mirror in the second direction when the mirror has moved beyond the determined first increment a number of the second increments equal to the second predetermined number of steps; and i) determining the second increment where the average peak amplitude of the received signal was the highest and moving the mirror to the determined second increment.

A method for aligning the first axis of a first mirror of a sensor. The method has the steps of:

a) moving the first mirror from a starting point a first predetermined number of steps in a first direction to a first location;

b) determining when the first mirror is in the first location the average peak amplitude of a signal received at a receiver connected to the first mirror;

c) moving the first mirror in a second direction which is opposite to the first direction in first increments each of a second predetermined number of steps and determining the average peak amplitude of the signal received at the receiving section at each of the first increments;

d) stopping movement of the first mirror in the second direction when the first mirror has moved a number of the first increments beyond the starting point equal to the first predetermined number of steps; and e) determining the first increment where the average peak amplitude of the received signal was the highest and moving the first mirror to the determined first increment.

An apparatus for aligning the axis of a mirror of a sensor. The apparatus has:

a) a digital processor; and b) a routine executed by the digital processor for:
  (i) moving the mirror from a starting point a first predetermined number of steps in a first direction to a first location;
  (ii) determining when the mirror is in the first location the average peak amplitude of a signal received at a receiver connected to the mirror;
  (iii) moving the mirror in a second direction which is opposite to the first direction in first increments each of a second predetermined number of steps and determining the average peak amplitude of the signal received at the receiving section at each of the first increments;
  (iv) stopping movement of the mirror in the second direction when the mirror has moved a number of the first increments beyond the starting point equal to the first predetermined number of steps; and
  (v) determining the first increment where the average peak amplitude of the received signal was the highest and moving the mirror to the determined first increment.

A solid fuel-fired steam generator that has:

a sensor for measuring in-situ and in real time the carbon content of the flue gas entrained fly ash that is produced from combustion occurring in the steam generator, the sensor comprising:

a mirror;

a digital processor; and a routine executed by the digital processor for:
  (i) moving the mirror from a starting point a first predetermined number of steps in a first direction to a first location;
  (ii) determining when the mirror is in the first location the average peak amplitude of a signal received at a receiver connected to the mirror;
  (iii) moving the mirror in a second direction which is opposite to the first direction in first increments each of a second predetermined number of steps and determining the average peak amplitude of the signal received at the receiving section at each of the first increments;
  (iv) stopping movement of the mirror in the second direction when the mirror has moved a number of the first increments beyond the starting point equal to the first predetermined number of steps; and
  (v) determining the first increment where the average peak amplitude of the received signal was the highest and moving the mirror to the determined first increment.

DESCRIPTION OF THE PREFERRED EMBODIMENT(S)

Figure 1:
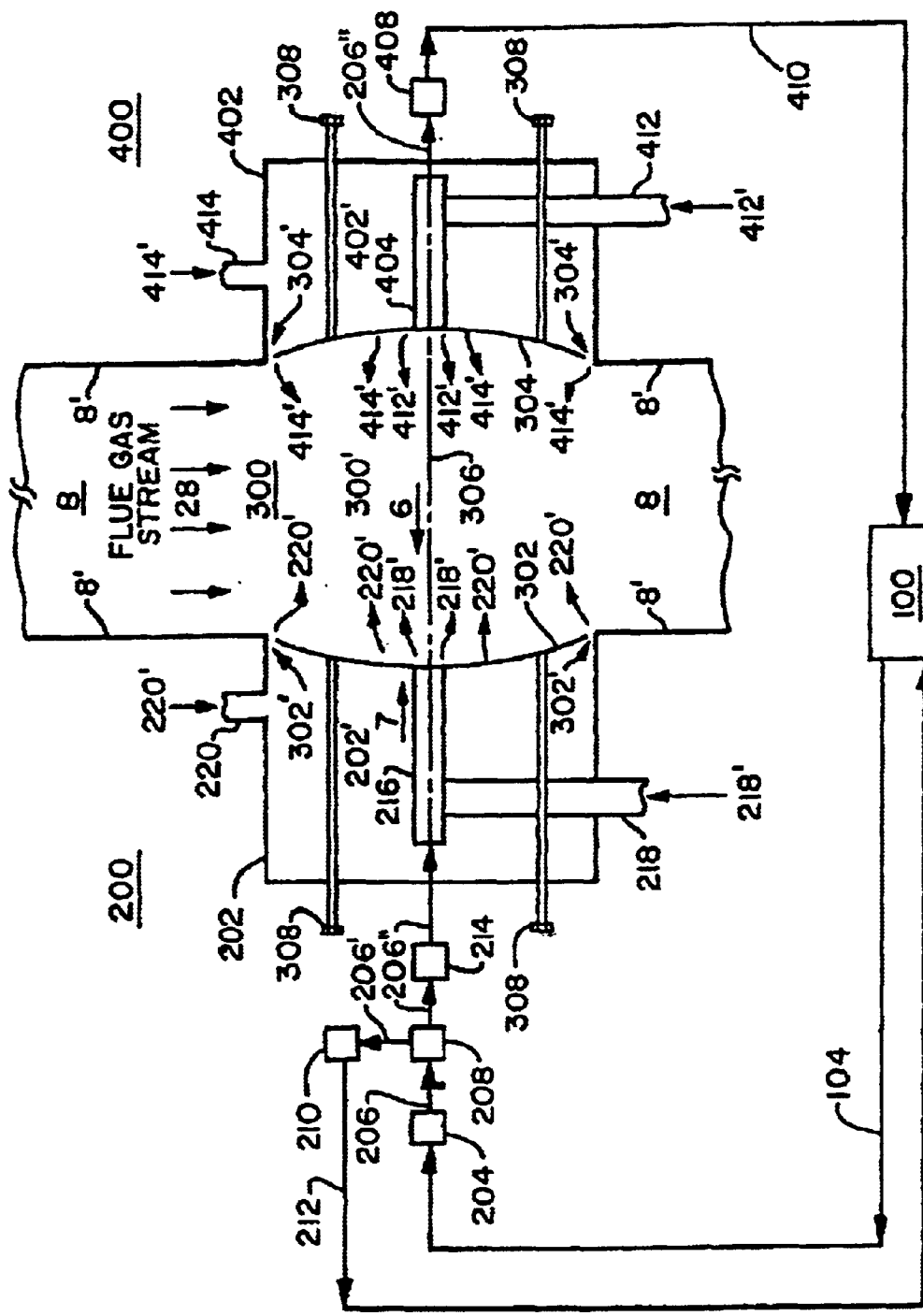
FIG. 1 shows the resonant cavity, and the intelligence, transmitting and receiving sections of the prior art Carbon in ash sensor.
Figure 1A:
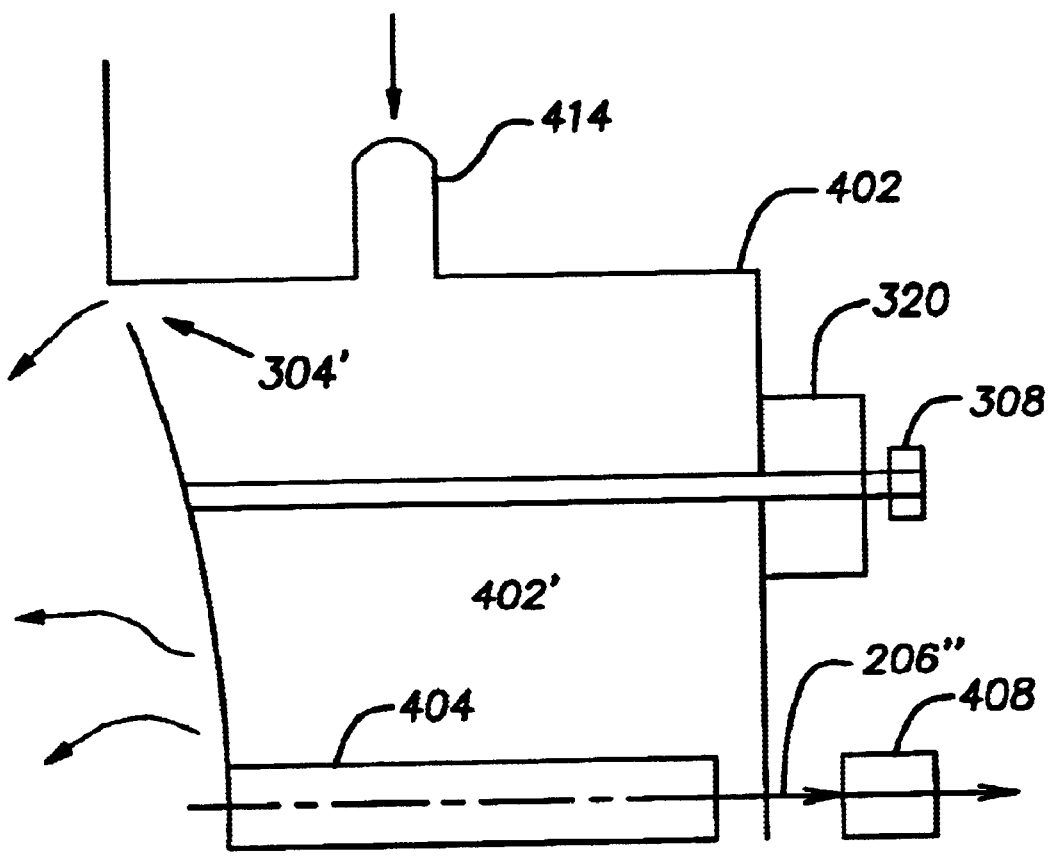
FIG. 1A is an enlargement of a portion of FIG. 1 showing a stepper motor threaded on the mirror alignment screw.
Figure 2:
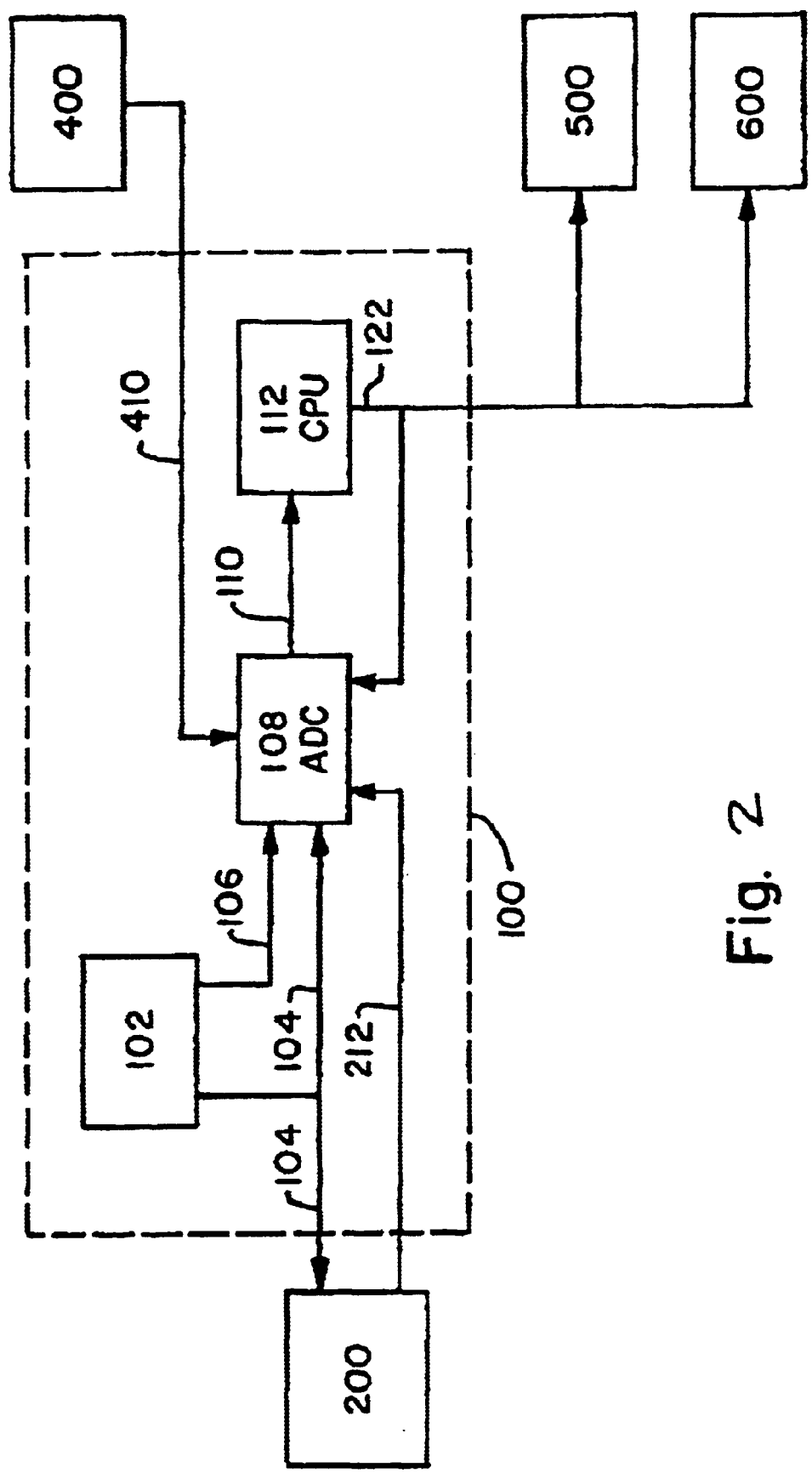
FIG. 2 shows a block diagram of the intelligence section of FIG. 1.
Figure 3:
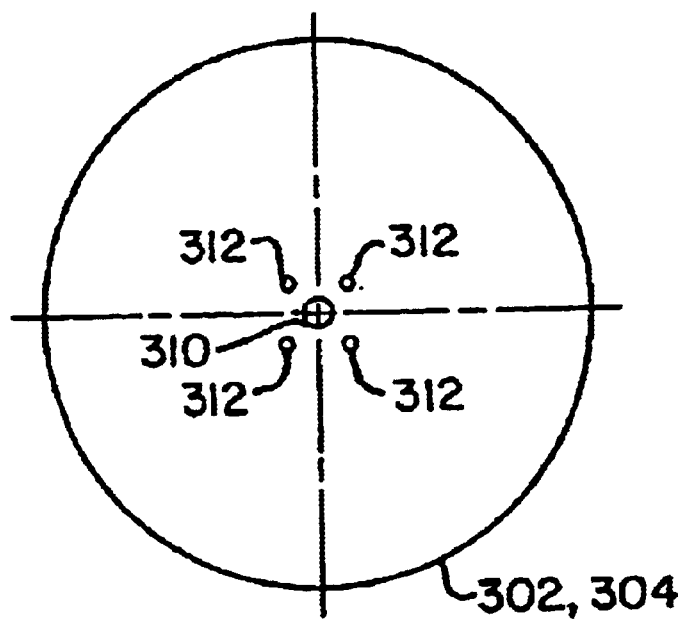
FIG. 3 shows a vertical sectional view of the reflecting surface of the mirrors shown in FIG. 1.
Figure 4:
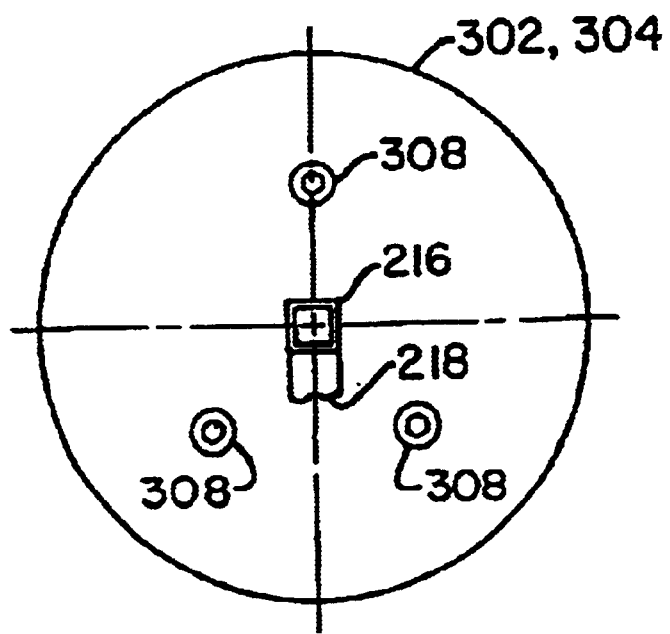
FIG. 4 shows a vertical sectional view of the nonreflecting surface of the mirrors shown in FIG. 1.
Figure 5A:
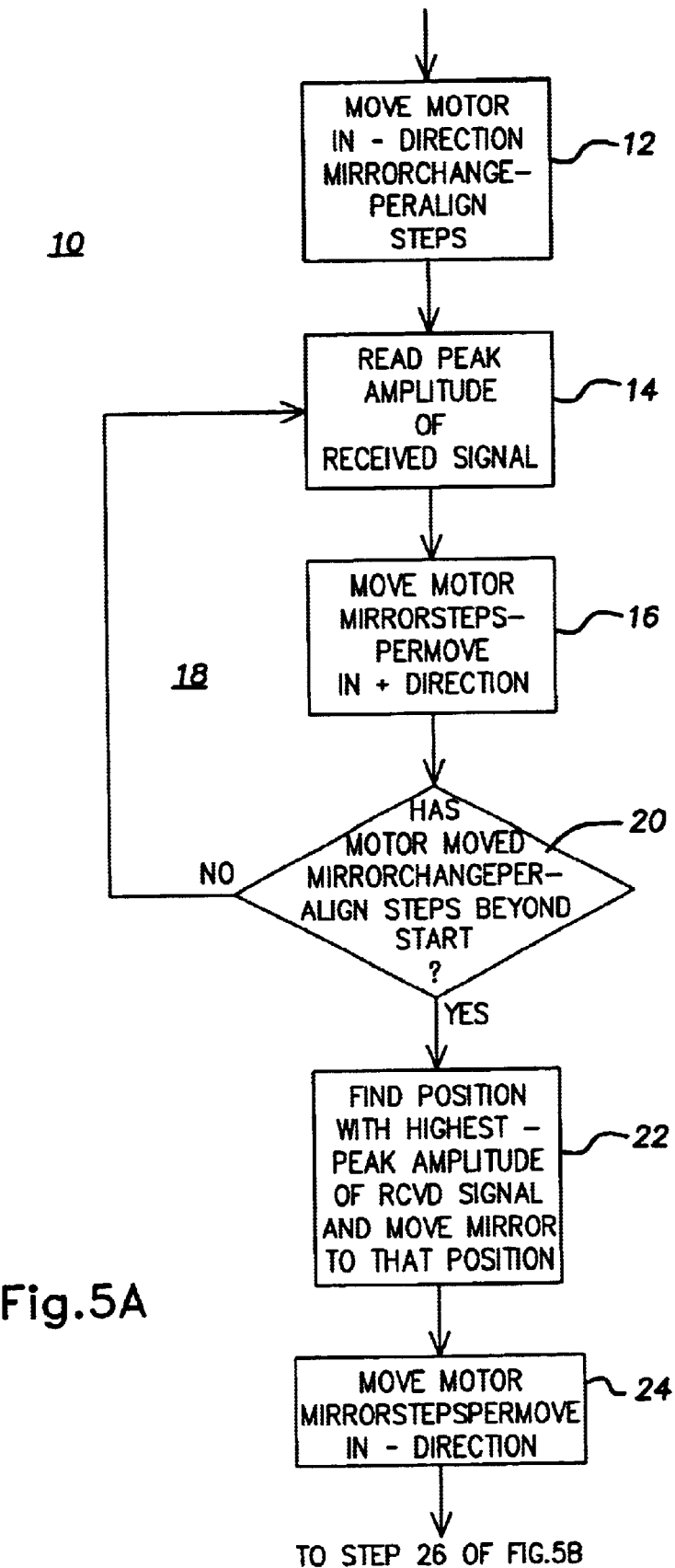
FIGS. 5A and B show a flowchart for the alignment method of the present invention.

Referring now to FIGS. 5A and B, there is shown a flowchart for the method 10 of the present invention that aligns the mirrors 302, 304. The method is executed in CPU 112. Every Alignmentinterval minutes the method 10 performs an alignment on one axis, X or Y, of one of mirrors 302, 304, where the Alignmentinterval in minutes is a configuration parameter set by the user of the system for detecting Carbon in fly ash.

The method 10 of the present invention aligns the X and Y axes of the mirrors 302, 304 in the following order:

a) align the Y axis of mirror 302;
b) align the Y axis of mirror 304;
c) align the X axis of mirror 302; and
d) align the X axis of mirror 304.

Therefore, the method of the present invention aligns any axis on a given mirror 302, 304 every four alignment cycles.

One alignment cycle will now be described with reference to the flow chart of FIGS. 5A and B. The first step 12 in the alignment method 10 of the present invention is to move a stepper motor that is threaded onto two of the three alignment screws 308 a predetermined number of steps, called MirrorChangeperAlign, in the negative direction. MirrorChangeperAlign is a configuration parameter which is set by the user of the Carbon in fly ash sensing system.

While positive and negative direction is strictly arbitrary, negative direction is used in the embodiment described herein of the alignment method of the present invention to represent clockwise rotation of the stepper motor. This rotation moves the edge of the mirror closer to the mounting plate. It should be appreciated that in the embodiment described herein the negative direction could have been used to represent the opposite rotation without changing the functionality of the alignment method of the present invention.

After performing step 12 the method 10 proceeds to step 14 wherein the peak amplitude of the signal at the receiving section 400 is read for a predetermined number of sweeps, called MirrorSweepsPerStep, of the oscillator 204 and there is calculated therefrom the average peak amplitude of the mirror at this location. MirrorSweepsPerStep is a configuration parameter that is set by the user of the system.

The method 10 then proceeds to step 16 where the stepper motor is moved a predetermined number of steps, called MirrorStepsPerMove, in the positive direction. MirrorStepsPerMove is a configuration parameter that is set by a user of the system. The method then repeats step 12. A loop 18 consisting of steps 16 and 14 is then repeated until decision block 20 has determined that the stepper motor is MirrorChangePerAlign steps in the positive direction beyond the starting point.

When the stepper motor reaches MirrorChangePerAlign steps in the positive direction beyond the starting point, the method 10 enters step 22 where the method 10 finds the MirrorChangePerAlign step that had the highest average peak amplitude and returns the stepper motor to that position.

Figure 5B:
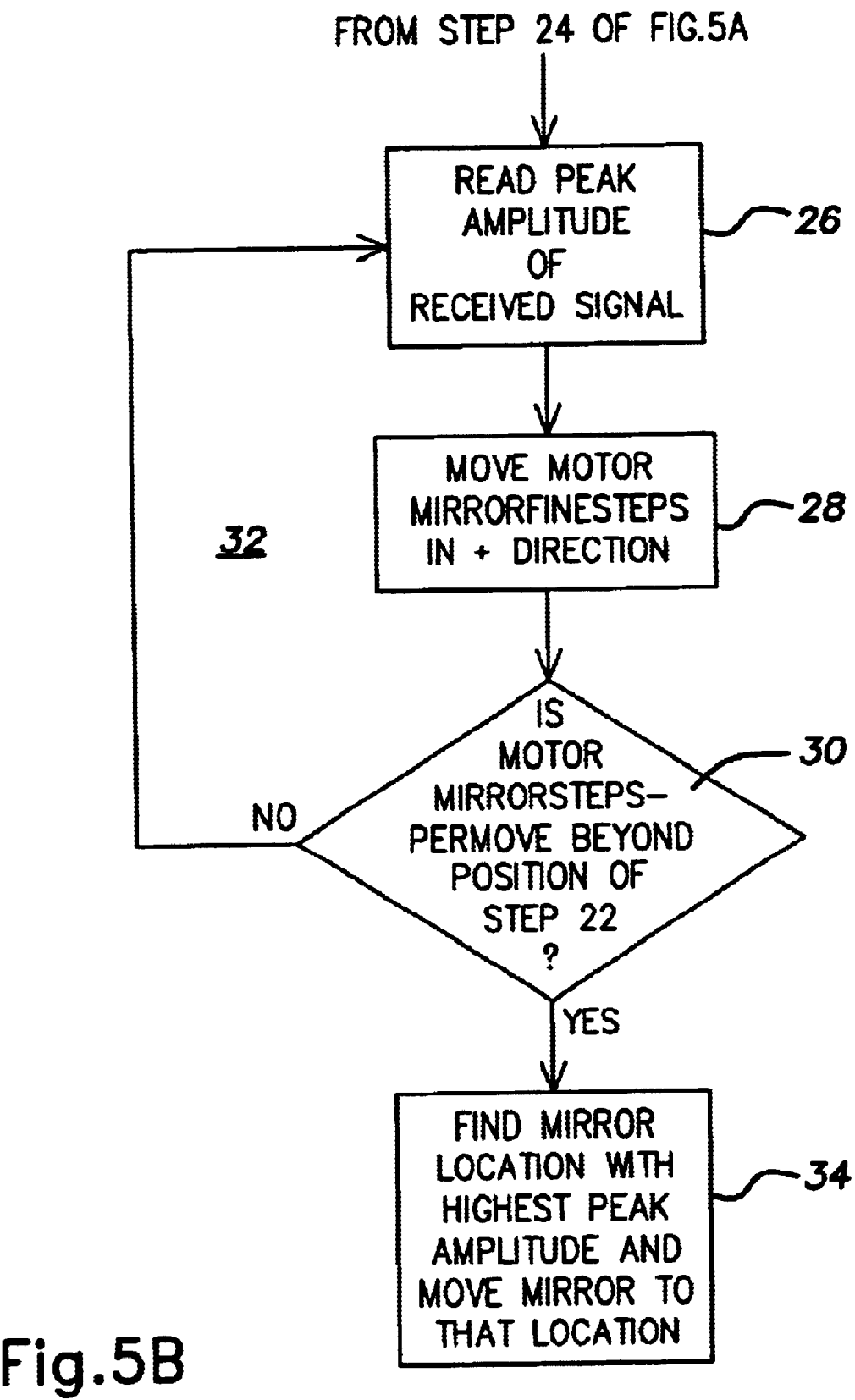

The method 10 then proceeds to step 24 where the stepper motor moves MirrorStepsPerMove in the negative direction. The method 10 then proceeds to step 26 on FIG. 5B where it reads for the predetermined number of oscillator sweeps the peak amplitude of the signal at the receiving section 400 and calculates the average peak amplitude of the mirror at this location.

After performing step 26 the method proceeds to step 28 where the stepper motor is moved a predetermined number of steps, called MirrorFineSteps, in the positive direction. A loop 32 consisting of steps 26 and 28 is then repeated until decision block 30 has determined that the stepper motor is MirrorsStepsPerMove beyond the position set in step 22.

When the stepper motor reaches MirrorsStepsPerMove beyond the position set in step 22, the method 10 enters step 34 where the method 10 finds the mirror position with the highest peak amplitude and returns the stepper motor and thus the mirror to that position.

It should be appreciated that the alignment method of the present invention minimizes the motion of the stepper motor as moving the motor is a relatively slow process as compared to the measurement performed by the sensor. Thus the present method maximizes the amount of time spent by the sensor in determining Carbon of the fly ash.

It should also be appreciated that the alignment method of the present invention finds the position of the mirror that produces the highest peak amplitude, within a range of MirrorChangePerAlign steps in either direction from the current position. The alignment method performs this function by first moving the mirror to the farthest position in this range in the negative (clockwise) direction. The method then move counter-clockwise, in steps of MirrorStepsPerMove, taking amplitude measurements at each stopping point, until it has reached the end of this range in the positive (counter-clockwise) direction.

It should further be appreciated that the alignment method of the present invention described above performs a first alignment of the mirror 302, 304 followed by a second alignment. The first alignment is performed in steps 10, 12, 14, 16 and 18 and is a coarse alignment of the mirror 302, 304. The second alignment is performed in steps 20 et seq. and is a fine alignment of the mirror 302, 304. As those skilled in the art will appreciate in certain instances it may only be necessary to perform the first alignment.

It should further also be appreciated that the user selected values for MirrorChangePerAlign, MirrorStepsPerMove, and MirrorFineSteps are application dependant. Typically the value for MirrorStepsPerMove is about 10% of the value for MirrorChangePerAlign and the value for MirrorFineSteps is about 10% of the value for MirrorStepsPerMove.

The movement of the mirrors 302, 304 is angular and therefore the farther apart the mirrors 302, 304 the smaller the value for MirrorChangePerAlign as a smaller angular change is needed to achieve the same movement of the signal received at the receiving section 400.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A method for aligning the first axis of a first mirror of a sensor comprising the steps of:
   a) determining when said first mirror is in a first location which is a first predetermined number of steps in a first direction from a starting point for said first mirror the average peak amplitude of a signal received at a receiver connected to said first mirror;
   b) moving said first mirror in a second direction which is opposite to said first direction in first increments each of a second predetermined number of steps and determining the average peak amplitude of said signal received at said receiving section at each of said first increments;
   c) stopping movement of said first mirror in said second direction when said first mirror has moved a predetermined number of said first increments beyond said starting point;
   d) determining said first increment where said average peak amplitude of said received signal was the highest and moving said first mirror to said determined first increment;
   e) moving said first mirror said second predetermined number of steps in said first direction to a second location and determining the average peak amplitude of said signal received at said receiving section at said second location;
   f) moving said first mirror in said second direction in second increments each of a third predetermined number of steps and determining the average peak amplitude of said signal received at said receiving section at each of said second increments;
   g) stopping movement of said first mirror in said second direction when said first mirror has moved beyond said determined first increment a predetermined number of said second increments; and
   h) determining said second increment where said average peak amplitude of said received signal was the highest and moving said first mirror to said determined second increment.

2. The method of claim 1 wherein in said first step of stopping movement of said first mirror in said second direction said predetermined number of first increments beyond said starting point is equal to said first predetermined number of steps.

3. The method of claim 1 wherein in said second step of stopping movement of said first mirror in said second direction said predetermined number of predetermined number of said second increments that said first mirror has moved beyond said first determined increment is equal to said second predetermined number of steps.

4. The method of claim 1 wherein:
   (i) in said first step of stopping movement of said first mirror in said second direction said predetermined number of first increments beyond said starting point is equal to said first predetermined number of steps; and
   (ii) in said second step of stopping movement of said first mirror in said second direction said predetermined number of predetermined number of said second increments that said first mirror has moved beyond said first determined increment is equal to said second predetermined number of steps.

5. The method of claim 1 furthering comprising before said step of determining when said first mirror is in said first location said average peak amplitude of said received signal the step of moving said first mirror from said starting point to said first location.

6. The method of claim 5 wherein in said first step of stopping movement of said first mirror in said second direction said predetermined number of first increments beyond said starting point is equal to said first predetermined number of steps.

7. The method of claim 5 wherein in said second step of stopping movement of said first mirror in said second direction said predetermined number of predetermined number of said second increments that said first mirror has moved beyond said first determined increment is equal to said second predetermined number of steps.

8. The method of claim 5 wherein:
   (i) in said first step of stopping movement of said first mirror in said second direction said predetermined number of first increments beyond said starting point is equal to said first predetermined number of steps; and
   (ii) in said second step of stopping movement of said first mirror in said second direction said predetermined number of predetermined number of said second increments that said first mirror has moved beyond said first determined increment is equal to said second predetermined number of steps.

9. The method of claim 1 wherein said sensor has a second mirror that has a first axis and said method aligns said first axis of said second mirror after said method finishes the alignment of said first axis of said first mirror.

10. The method of claim 9 wherein said alignment of said first axis of said second mirror comprises the execution of steps (a) to (h) of claim 1.

11. The method of claim 9 wherein said first mirror has a second axis and said second mirror has a second axis and said method aligns said first and second mirrors in a sequence of first aligning said first axis of said first mirror, then said first axis of second mirror, then said second axis of said first mirror and then said second axis of said second mirror.

12. The method of claim 11 wherein said sequence is repeated at a predetermined frequency.

13. A method for aligning the axis of a mirror of a sensor comprising the steps of:
   a) moving said mirror from a starting point a first predetermined number of steps in a first direction to a first location;
   b) determining when said mirror is in said first location the average peak amplitude of a signal received at a receiver connected to said mirror;
   c) moving said mirror in a second direction which is opposite to said first direction in first increments each of a second predetermined number of steps and determining the average peak amplitude of said signal received at said receiving section at each of said first increments;
   d) stopping movement of said mirror in said second direction when said mirror has moved a number of said first increments beyond said starting point equal to said first predetermined number of steps;
   e) determining said first increment where said average peak amplitude of said received signal was the highest and moving said mirror to said determined first increment;
   f) moving said mirror said second predetermined number of steps in said first direction to a second location and determining the average peak amplitude of said signal received at said receiving section at said second location;

g) moving said mirror in said second direction in second increments each of a third predetermined number of steps and determining the average peak amplitude of said signal received at said receiving section at each of said second increments;

h) stopping movement of said mirror in said second direction when said mirror has moved beyond said determined first increment a number of said second increments equal to said second predetermined number of steps; and i) determining said second increment where said average peak amplitude of said received signal was the highest and moving said mirror to said determined second increment.

14. A method for aligning the first axis of a first mirror of a sensor comprising the steps of:

a) moving said first mirror from a starting point a first predetermined number of steps in a first direction to a first location;

b) determining when said first mirror is in said first location the average peak amplitude of a signal received at a receiver connected to said first mirror;

c) moving said first mirror in a second direction which is opposite to said first direction in first increments each of a second predetermined number of steps and determining the average peak amplitude of said signal received at said receiving section at each of said first increments;

d) stopping movement of said first mirror in said second direction when said first mirror has moved a number of said first increments beyond said starting point equal to said first predetermined number of steps; and e) determining said first increment where said average peak amplitude of said received signal was the highest and moving said first mirror to said determined first increment.

15. The method of claim 14 further comprising the steps of:

a) moving said first mirror said second predetermined number of steps in said first direction to a second location and determining the average peak amplitude of said signal received at said receiving section at said second location;

b) moving said first mirror in said second direction in second increments each of a third predetermined number of steps and determining the average peak amplitude of said signal received at said receiving section at each of said second increments;

c) stopping movement of said first mirror in said second direction when said first mirror has moved beyond said determined first increment a number of said second increments equal to said second predetermined number of steps; and d) determining said second increment where said average peak amplitude of said received signal was the highest and moving said first mirror to said determined second increment.

16. The method of claim 14 wherein said sensor has a second mirror that has a first axis and said method aligns said first axis of said second mirror after said method finishes the alignment of said first axis of said first mirror.

17. The method of claim 16 wherein said alignment of said first axis of said second mirror comprises the execution of steps (a) to (e) of claim 14.

18. The method of claim 14 wherein said first mirror has a second axis and said second mirror has a second axis and said method aligns said first and second mirrors in a sequence of first aligning said first axis of said first mirror, then said first axis of second mirror, then said second axis of said first mirror and then said second axis of said second mirror.

19. The method of claim 18 wherein said sequence is repeated at a predetermined frequency.

20. Apparatus for aligning the axis of a mirror of a sensor, said apparatus comprising:

a) a digital processor; and b) a routine executed by said digital processor for:

(i) moving said mirror from a starting point a first predetermined number of steps in a first direction to a first location;

(ii) determining when said mirror is in said first location the average peak amplitude of a signal received at a receiver connected to said mirror;

(iii) moving said mirror in a second direction which is opposite to said first direction in first increments each of a second predetermined number of steps and determining the average peak amplitude of said signal received at said receiving section at each of said first increments;

(iv) stopping movement of said mirror in said second direction when said mirror has moved a number of said first increments beyond said starting point equal to said first predetermined number of steps; and (v) determining said first increment where said average peak amplitude of said received signal was the highest and moving said mirror to said determined first increment.

21. The apparatus of claim 20 further comprising a motor connected to said axis for moving said mirror.

22. The apparatus of claim 20 wherein said routine further comprises the steps of:

(i) moving said mirror said second predetermined number of steps in said first direction to a second location and determining the average peak amplitude of said signal received at said receiving section at said second location;

(ii) moving said mirror in said second direction in second increments each of a third predetermined number of steps and determining the average peak amplitude of said signal received at said receiving section at each of said second increments;

(iii) stopping movement of said mirror in said second direction when said mirror has moved beyond said determined first increment a number of said second increments equal to said second predetermined number of steps; and (iv) determining said second increment where said average peak amplitude of said received signal was the highest and moving said mirror to said determined second increment.

23. The apparatus of claim 22 further comprising a motor connected to said axis for moving said mirror.

24. A solid fuel-fired steam generator comprising:

a sensor for measuring in-situ and in real time the carbon content of the flue gas entrained fly ash that is produced from combustion occurring in said steam generator, said sensor comprising:

a mirror;

a digital processor; and a routine executed by said digital processor for:

(i) moving said mirror from a starting point a first predetermined number of steps in a first direction to a first location;

(ii) determining when said mirror is in said first location the average peak amplitude of a signal received at a receiver connected to said mirror;

(iii) moving said mirror in a second direction which is opposite to said first direction in first increments each of a second predetermined number of steps and determining the average peak amplitude of said signal received at said receiving section at each of said first increments;

(iv) stopping movement of said mirror in said second direction when said mirror has moved a number of said first increments beyond said starting point equal to said first predetermined number of steps; and (v) determining said first increment where said average peak amplitude of said received signal was the highest and moving said mirror to said determined first increment.

25. The steam generator of claim 24 wherein said sensor further comprises a motor connected to said axis for moving said mirror.

26. The steam generator of claim 24 wherein said routine executed by said digital processor in said sensor further comprises the steps of:

(i) moving said mirror said second predetermined number of steps in said first direction to a second location and determining the average peak amplitude of said signal received at said receiving section at said second location;

(ii) moving said mirror in said second direction in second increments each of a third predetermined number of steps and determining the average peak amplitude of said signal received at said receiving section at each of said second increments;

(iii) stopping movement of said mirror in said second direction when said mirror has moved beyond said determined first increment a number of said second increments equal to said second predetermined number of steps; and (iv) determining said second increment where said average peak amplitude of said received signal was the highest and moving said mirror to said determined second increment.

27. The steam generator of claim 26 wherein said sensor further comprises a motor connected to said axis for moving said mirror.

* * * * *